(12) United States Patent
Arita

(10) Patent No.: US 8,083,844 B2
(45) Date of Patent: Dec. 27, 2011

(54) CHEMICALLY-CURING TYPE GLASS IONOMER CEMENT

(75) Inventor: Kenji Arita, Tokushima (JP)

(73) Assignee: The University of Tokushima, Tokushima (JP)

( * ) Notice: Subject to any disclaimer, the term of this patent is extended or adjusted under 35 U.S.C. 154(b) by 570 days.

(21) Appl. No.: 12/298,154

(22) PCT Filed: Apr. 27, 2007

(86) PCT No.: PCT/JP2007/058885
§ 371 (c)(1),
(2), (4) Date: Oct. 23, 2008

(87) PCT Pub. No.: WO2007/125930
PCT Pub. Date: Nov. 8, 2007

(65) Prior Publication Data
US 2009/0118391 A1    May 7, 2009

(30) Foreign Application Priority Data
Apr. 24, 2006  (JP) ................................. 2006-119051

(51) Int. Cl.
*A61K 6/033* (2006.01)
*A61K 6/027* (2006.01)
*A61L 27/00* (2006.01)

(52) U.S. Cl. ......... 106/35; 433/1; 433/228.1; 623/23.62

(58) Field of Classification Search ........... 433/1, 228.1; 623/23.62; 106/35
See application file for complete search history.

(56) References Cited

U.S. PATENT DOCUMENTS
2005/0260269 A1   11/2005   Engelbrecht et al.

FOREIGN PATENT DOCUMENTS
JP   5-168692     7/1993
JP   2001-354509  12/2001

OTHER PUBLICATIONS

Luas et al, "Toughness, bonding and fluoride-release propeties of hydroxyapatite-added glass ionomer cemt", Biomaterials, 24 (2003), pp. 3787-3794.*

A.U.J. Yap et al., "Experimental studies on a new bioactive material", Biomaterials, vol. 23, 2002, pp. 955-962, XP-002589077.

Extended European Search Report for corresponding EP Application No. 07742320.0-1219, Jul. 12, 2010.

(Continued)

*Primary Examiner* — Carol M Koslow
(74) *Attorney, Agent, or Firm* — Ditthavong Mori & Steiner, P.C.

(57) ABSTRACT

This invention provides quality and safe chemically-curing type GIC that solves all the disadvantages of light-curing type GIC, and has mechanical strength not lower but higher than that of light-curing type GIC and, in addition to this, the original features and advantages of GIC. The chemically-curing type glass ionomer cement according to the present invention includes porous and particulate hydroxy apatite that has a means diameter of not less than 0.6 μm and less than 100 μm and a large specific surface, and is added and mixed into the glass ionomer cement.

9 Claims, 2 Drawing Sheets

IMAGE OF HAp100 (FINE) MAGNIFIED BY 15,000 TIMES

OTHER PUBLICATIONS

Empizo, et al., "Strengthening the Matrix of a Glass Ionomer Cement Using Hydroxyapatite", Pediatric Dentistry Journal, vol. 39, No. 2, 2001, p. 338.

Arita et al., The Effect of Adding Hydroxyapatite Whiskers on the Flexural Strength of Glass-Ionomer Cement (Part 1), Pediatric Dentistry Journal, vol. 38, No. 2, 2000, p. 368.

Yamamoto, "Fundamental Study about the Synthetic Hydroxyapatite-Polyacrylic Acid Composite Material Based on Glass Ionomer Cement Medium", The Journal of the Japanese Society for Dental Materials and Devices, vol. 3, No. 6, 1984, pp. 787 to 796, p. 789, III-1; p. 790; Fig. 4.

Gu et al., "Effects of incorporation of $HA/ZrO_2$ into glass ionomer cement (GIC)", Biomaterials, vol. 26, No. 7, 2005, pp. 713-720.

Suwa, "Development of Bioceramics for Medical Filling Material and Prosthetic Material", New-ceramics, No. 10, pp. 11-17, p. 16, 2.3, 1994, Japan.

Arita et al., "The Effect of Adding Hydroxyapatite on the Flexural Strength of Glass Ionomer Cement", Dental Materials Journal, vol. 22, No. 2, 2003, pp. 126-136.

Lucas et al., "Toughness, bonding and fluoride-release properties of hydroxyapatite-added glass ionomer cement", Biomaterials, vol. 24, 2003, pp. 3787-3794.

* cited by examiner

IMAGE OF HAp100 MAGNIFIED BY 10,000 TIMES

IMAGE OF HAp100 (FINE) MAGNIFIED BY 15,000 TIMES

IMAGE OF HAp200 MAGNIFIED BY 15,000 TIMES

CHEMICALLY-CURING TYPE GLASS IONOMER CEMENT

TECHNICAL FIELD

This invention relates to glass ionomer cement that is mainly used for dentistry. More particularly, this invention relates to glass ionomer cement that has mechanical strength such as bending strength and tensile strength equal to or higher than that of light-curing type glass ionomer cement.

BACKGROUND ART

The events are as follows which spread the use of glass ionomer cement (abbreviated as "GIC" in this specification).
(1) Phosphate cement before 1967. This phosphate cement has features of engagement strength with dentin and coalescence strength. In addition to this,
(2) carboxylate cement, which D. C. Smith developed in 1968. This carboxyl cement has a feature of adhesive strength to dentin. However, it was seen that carboxyl cement had disadvantages such as lack of mechanical strength, and large thermal expansion difference between dentin and this cement. For this reason, in order to solve the disadvantages,
(3) GIC was introduced by A. D. Wilson in 1971.

This GIC has advantages and features that cannot be obtained by other materials. The advantages and features are as follows.
(1) Low irritation to and biological affinity for dental pulp.
(2) Secondary dental caries suppression effect and antibacterial activity by release and recharge of fluorine ion.
(3) High adhesiveness to dentin and metal (chemical adhesion).
(4) Elimination of tooth surface treatment (acid etching) in use by this high adhesiveness.
(5) Close thermal expansion coefficient to dentin.
(6) GIC is translucent after cured. This provides an excellent aesthetic feature and the like.

The GIC in the introduction was chemically-curing type (or chemically-polymerized type) GIC that was used by reacting silicate cement (for fore tooth restorative filling) powder or glass powder with polymeric acid principally composed of acid such as polycarboxylic acid in water-existing conditions. It was said that silicate cement had high dental caries protection from long ago.

However, it was seen that the GIC had disadvantages of embrittlement caused by its water sensitivity (high solubility) in the early curing stage, low bending strength (fragility) and the like. For this reason, it was required to prepare the GIC with careful attention in clinical use of prosthetic adhesion, filling and the like.

Afterward, in order to increase mechanical strength, resin group GIC was developed which was obtained by adding and mixing a resin component into the aforementioned chemically-curing type GIC. Furthermore, light-curing type (photo-polymerized type) GIC became commercially practical which was obtained by employing a photo-polymerized type resin and a photo polymerization catalyst and was quickly cured. Today, among various types of commercially available GIC such as chemically-curing type GIC and resin group GIC, the light-curing type GIC is widely used and is in the mainstream.

However, in this light-curing type GIC, the aforementioned original advantages decrease. The following disadvantages are known.

(1) Added resin causes secondary caries and irritation to dental pulp, and reduces biological affinity for dental pulp.
(2) The slow-release amount of fluoride decreases.
(3) Tooth surface treatment (acid etching) is required in adhesion.
(4) Since a light irradiation device is required, light-curing type GIC is not convenient and cannot be used in developing countries, and the like.

In order to solve the disadvantages of the resin group GIC and light-curing type GIC, technology is under development to improve the mechanical strength of GIC without using resins. For example, technology is known which adds and mixes apatite fiber into conventional glass powder for GIC to improve the strength of chemically-curing type GIC (see Japanese Patent Laid-Open Publication TOKUKAI No. 2001-354509; Dental Materials Journal, Vol. 22 (No. 2), 126-136, 2003, and Biomaterials, Vol. 24, 3787-3794, 2003). Also, technology is developed which adds apatite nanoparticles of 200 nm or less.

However, in the case of the aforementioned chemically-curing type GIC, the reinforcement (improvement) by apatite addition and mixture is about 30% in mechanical strength. This is about 40% lower as compared with the reinforcement (improvement) by light-curing type GIC. For this reason, light-curing type GIC is widely used and is in the mainstream today. The aforementioned chemically-curing type GIC cannot be evaluated as a substitute for light-curing type GIC.

Also, in the case of GIC of US patent publication US 2005/0260269, hard, strong and fine apatite crystalline particles are added which are nanoparticles that are chemically formed by solution deposition (wet process). This GIC has a disadvantage in that curing time cannot be shortened to the extent of actually available use. In addition to this, though crystals of apatite that are hard nanoparticle are used as a filler (reinforcing member), the crystals of apatite cannot reinforce the mechanical strength of GIC in a cured state.

SUMMARY OF THE INVENTION

The inventor does not add hydroxy apatite as a hard filler into GIC. In this present invention, I focus that GIC reacts quickly with teeth, which is apatite, on the boundary and creates new products, and that the new products firmly are bonded onto the surfaces of the teeth. I achieve this state over the entire GIC. Thus, I have successfully improved the mechanical strength of GIC in the cured state. That is, particular hydroxy apatite is added and mixed to create a new compound on the boundary of this hydroxy apatite and GIC so that the cured GIC is entirely reinforced. Since hydroxy apatite quickly reacts with GIC on the boundary, in addition to reduction of GIC curing time, I have successfully reinforced the mechanical strength. That is, I consider the facts that hydroxy apatite makes up 95% of dentin, that GIC chemically reacts with dentin and is strongly bonded together, and that the bonded part of GIC is stronger than the other parts. Based on these facts, I add and mix particular hydroxy apatite into GIC to lead occurrence of the reaction that occurs on the boundary between dentin and GIC over the entire GIC. Thus, in addition to reduction of GIC curing time, I have successfully reinforced the mechanical strength.

Therefore, it is an issue of this invention to provide quality and safe chemically-curing type GIC that solves all the aforementioned disadvantages of light-curing type GIC, and has mechanical strength not lower but higher than that of light-curing type GIC and, in addition to this, the aforementioned original features and advantages of GIC.

Also, in recent years, the concept of Minimal Intervention (MI) is globally spreading in dentistry. GIC is used getting more frequently which is a dentin bonding material and has high histocompatibility. In particular, chemically-curing type GIC is adopted as a restoration material of Atraumatic Restorative Treatment (ART) in developing countries by WHO. Chemically-curing type GIC fills teeth without scraping teeth. Thus, chemically-curing type GIC obtains a high effect and high evaluation. For this reason, it is an urgent global issue to provide the above quality and safe chemically-curing type GIC. This invention provides good news to all humanity.

In this invention, porous and particulate hydroxy apatite that has a mean diameter of not less than 0.6 μm and less than 100 μm is added and mixed into GIC that is obtained by mixing glass powder and polyacrylic acid solution and curing the mixed glass powder and polyacrylic acid solution. Thus, I have successfully reduced curing time in addition to remarkable improvement or reinforcement of chemically-curing type GIC.

To resolve the foregoing issues, this invention provides the following construction.

(1) GIC is provided with porous and particulate hydroxy apatite that has a mean diameter of not less than 0.6 μm and less than 100 μm and is added and mixed into the GIC. In order to accelerate reaction between hydroxy apatite and GIC, the porous and particulate hydroxy apatite has a large specific surface.

(2) Hydroxy apatite is preferably used which has ultra-fine particles of identical hydroxy apatite that are adhered on the surface of the hydroxy apatite.

(3) The amount of the hydroxy apatite is preferably 5.0 to 35% by weight relative to glass powder that is included in the GIC.

(4) The mean diameter of the hydroxy apatite that is added into the GIC is preferably 1 to 50 μm, and more preferably 3 to 20 μm.

(5) GIC is used which is obtained by mixing glass powder and polyacrylic acid solution and curing the mixed glass powder and polyacrylic acid solution.

(6) The GIC according to the present invention is used for dentistry, bone therapy in medicine and veterinary medicine fields, bone tissue restoration or bone tissue regeneration.

Chemically-curing type GIC according to the present invention provides, in addition to resolution of all the aforementioned disadvantages of light-curing type GIC, ideal features in that its mechanical strength is improved additionally in that curing time is reduced. These ideal features cannot be provided by conventional chemically-curing type GIC. The reason to provide these ideal features is that the chemically-curing type GIC according to the present invention includes porous hydroxy apatite that has a particular mean diameter. GIC quickly reacts with dentin, which is HAp, on the boundary, and the GIC and the dentin is firmly and strongly bonded together. In the present invention, the mechanical strength of GIC is reinforced by using this special phenomenon. The present invention is different from hardening of GIC by adding hard HAp as a filler. In this invention, HAp to be added is particular particulate HAp that has a large specific surface in the porous state, in order that teeth may quickly react with GIC, so that the particulate HAp quickly reacts with GIC. Thus, the mechanical strength is improved. In the GIC according to the present invention, the particulate HAp that is mixed is dispersed in the hardened state. In addition to this, the dispersed HAp quickly reacts with GIC, and the HAp and the GIC are strongly and firmly bonded together. Thus, the mechanical strength is improved. In particular, since the apatite to be added into GIC is the particular particulate HAp that is in the porous state that increases the specific surface of the particular particulate HAp, the reactivity between the apatite and the GIC is very high. Thus, curing time is remarkably reduced, and the mechanical strength is reinforced.

In this connection, the strength of GIC according to a later-described example 1 is increased to 37.3 MPa in a 15-minute-after three-point bending test. This value is about 2.4 times stronger than the strength 15.4 MPa of photo-polymerized type GIC without added apatite in the 15-minute-after three-point bending test. Also, this value is 40% stronger than the strength 25.6 MPa of GIC according to a comparative example 3 with added non-porous HAp.

In addition to this, since GIC according to the present invention is quickly and chemically cured to an excellent mechanical strength, as compared with light curing resins, the GIC has excellent properties described in (a) to (f) that are required for clinical model dentistry.

(a) As compared with a light-curing resin with a resin mixed together, the GIC has secondary dental caries suppression and antibacterial activity by release and recharge of fluorine ion.

(b) The GIC exhibits dentin bondability (chemical bonding) that does not require tooth surface treatment (acid etching).

(c) As compared with light curing resin, the GIC provides low irritation to and biological affinity for dental pulp. The reason is that non-stimulus GIC is added into non-stimulus hydroxy apatite.

(d) The GIC has a close thermal expansion coefficient to dentin.

(e) The mechanical strength of the GIC is equivalent to light-curing type GIC.

(f) The mechanical strength of the GIC rises to the extent that is effective after 15 minutes or shorter at room temperature in clinical dentistry.

Also, in recent years, the concept of Minimal Intervention (MI) is globally spreading in the dentistry field. GIC is used getting more frequently which is a dentin-bonding material and has high histocompatibility. This invention can satisfy this worldwide demand.

Also, chemically-curing type GIC is adopted as a restoration material of Atraumatic Restorative Treatment (ART) in developing countries by WHO. Chemically-curing type GIC fills teeth without scraping teeth. Thus, chemically-curing type GIC obtains a high effect and high evaluation. This invention responds to this WHO recommendation or requests.

Also, GIC according to this invention is widely applicable and useful not only as a material in the dentistry field but also a material for bone therapy and restoration or regeneration of bone tissue in the medicine and veterinary medicine fields.

DESCRIPTION OF THE PREFERRED EMBODIMENT(S)

Following description will describe embodiments according to this invention.

Hydroxy apatite is added into glass ionomer cement (GIC) of the present invention, and the GIC is cured. GIC is composed of powder for GIC such as aluminosilicate glass, and a reaction liquid for GIC such as polycarboxylic acid solution.

[Powder for GIC]

Various types of commercially-available glass powder for chemically-curing type GIC can be used as the powder for GIC.

[Reaction Liquid for GIC]

Also, as the reaction liquid, a solution is employed which is mainly composed of polyacrylic acid, distilled water, carboxylic acid for curing chemical reactions, and the like. However, as this reaction liquid, all types of already commercially available reaction liquid for GIC, and additionally all types of carboxylic acid, which will be developed as reaction liquid for GIC, can be used.

[Hydroxy Apatite]

Particular hydroxy apatite is added into GIC of the present invention. Hereinafter, hydroxy apatite is abbreviated as "HAp." In addition of this HAp, in consideration of curing time of GIC, the thermal expansion coefficient difference between GIC and dentin, biological affinity, fluoride slow-release property and the like, particulate and porous HAp [$Ca_{10}(PO_4)_6(OH)_2$] is employed which has a particular mean diameter. As this HAp, HAp is preferably used which has ultra-fine hydroxy apatite particles of 3 to 500 nm that are adhered on the surface of the HAp.

In this connection, if the mean diameter of particulate HAp is too large or too small, the mechanical strength of the particulate HAp decreases. In addition, if the mean diameter of HAp is too small, curing time increases. Accordingly, in consideration of mechanical strength and curing time, HAp is used which has a mean diameter of not less than 0.6 μm and less than 100 μm, preferably 1 to 50 μm, and more preferably 3 to 20 μm. In addition to this, in order to improve reactivity, HAp is used which is porous and has a large specific surface. HAp is preferably used which has a specific surface of 20 to 100 $m^2/g$. If the specific surface of HAp is small, reactivity with GIC decreases.

[The Mixture Amount of HAp]

Added and mixed particulate HAp provides reinforcement and improvement in the mechanical strength of a matrix that holds GIC glass component particles in a cured material. In consideration of this, the addition/mixture amount of particulate HAp relative to powder for GIC is less than 50% by weight, preferably about 5 to 35% by weight, more preferably about 5 to 30% by weight, and most preferably about 10% by weight.

[Chemically-Curing Processes]

(1) HAp is added and mixed into powder for GIC, and is then sufficiently mixed.

(2) Subsequently, reaction liquid for GIC is added and mixed into the mixed powder of the powder for GIC and HAp, and is then sufficiently kneaded together. At this process, P/L as the ratio of the mixed powder to the reaction liquid for GIC (the ratio by weight of (the mixed powder)/(the reaction liquid)) is 3.6. It should be appreciated that P/L can fall within a range of 2 to 4.

(3) The thus-obtained kneaded material starts being cured. After the kneaded material is left standing at room temperature, body temperature or the like for about 5 to 60 minutes or preferably about 10 to 30 minutes, or about 5 to 60 minutes or preferably about 10 to 30 minutes elapse, the kneaded material is cured to a desired mechanical strength.

Examples according to the present invention are now given to specifically describe the construction and effects of this invention. However, this invention is not limited to only these examples.

EXAMPLE 1 AND COMPARATIVE EXAMPLES 1 to 5

Chemically-curing type GIC with added HAp is cured in the following processes.

As reaction liquid for GIC and powder for GIC, glass powder of commercially-available chemically-curing type GIC "FujiIXGP [manufactured by GC Corp. (Japan)]" (hereinafter referred to as "IX powder", and reaction liquid (hereinafter referred to as "IX liquid") are used.

As HAp to be added into the glass poder, the following four types of HAp (1) to (4) are used. That is, HAp wisker (comparative example 1), HAp100 (comparative example 2), HAp100 (fine) (example 1) and HAp200 (comparative example 3) are used, and GIC according to the example 1 of the present invention and the comparative examples 1 to 3 are cured.

(1) Comparative Example 1

In this comparative example, although apatite is added into GIC, as the apatite, HAp wisker [offered from Mitsubishi Materials Corp. (Japan)] is used which is non-porous crystal fiber.

(2) Comparative Example 2

Also in this comparative example, although apatite is added into GIC, as the apatite, HAp is used which has a large mean particle diameter that does not meet the scope of the present invention. That is, HAp100 [manufactured by Taihei Chemical Industrial Co., Ltd. (Japan); mean diameter of about 100 to 170 μm, fragile powder] is used. FIG. 1 shows an electron micrograph of this HAp100 magnified by 10,000 times.

(3) Example 1

This example is an example according to the present invention. In this example, as HAp to be added into GIC, HAp100 (fine), which is used in the comparative example 2, is prepared by pulverization into ultra-fine particles with a mean particle diameter of 3 to 20 μm by using an automatic mill (electric dancing mill, Nitto Kagaku Co., Ltd). The thus-prepared HAp100 (fine) is used. This hydroxy apatite is porous, and the ultra-fine particles of several nanometers to several hundreds nanometers are adhered on the surface of the hydroxy apatite. FIG. 2 shows an electron micrograph of this HAp100 (fine) magnified by 15,000 times.

(4) Comparative Example 3

In this comparative example, as apatite to be added into GIC, Hap200 is used which is composed of secondary particles that are formed of agglomerating hexagonal columnar crystals. Hap200 does not meet the scope of the present invention. This apatite is manufactured by Taipei Chemical Industrial Co., Ltd (Japan). The mean particle diameter of the apatite is about 5 to 20 μm. The shorter diameter of and the longer diameter of primary particle are 0.3 to 0.5 μm and about 2 to 3 μm, respectively. FIG. 3 shows an electron micrograph of this HAp200 magnified by 15,000 times.

(5) Comparative Example 4

In this comparative example, chemically-curing type GIC is not used, but, as GIC, commercially-available light-curing type glass ionomer cement IILC EM [manufactured by GC Corp. (Japan)] is used.

Each of the aforementioned four types of HAp is added and mixed into IX powder at 8% by weight relative to the IX powder. This addition/mixture provides sample powder. Subsequently, IX liquid is added and mixed into each type of sample powder so that P/L ((mixed powder)/(reaction liquid)) is 3.6. After that, IX liquid and each type of sample powder are kneaded. Six sample materials are made for each of example and comparative examples in this manner.

Curing and Testing Methods of GIC in Example and Comparative Examples (1) IX powder, IX liquid, and HAp are measured by using an electronic balance [manufactured by Satorius Corp. (Germany)].
(2) The measured IX powder and HAp powder are mixed by using an automatic mixer (vortex) for one minute.
(3) A separation material (SURE SEP) is applied on a mold of stainless steel alloy (3.0 mm×3.0 mm×25.0 mm) with a small brush, and is then extended and thinned with air.
(4) The mixed powder and the IX liquid are kneaded by using a plastic spatula on a paper mixing pad for 45 seconds.
(5) Subsequently, this kneaded material is aspirated into a syringe (a kind of injector), and is then injected into the mold. In this process, the mold is pressed by a plugger that brings neither air bubbles nor clearances, then is placed on a glass mixing plate.
(6) The mold is pressed by a weight (500 g) so that a transparent strip is sandwiched between the mold and the weight, and is then left standing for ten minutes at room temperature.
The GIC is cured in this state.
(7) The sample material is picked up from the mold, and is then left standing in conditions of 37° C., humidity 100% (the sample material is wrapped in a filter paper sheet dampened with water) for 50 minutes.
This process applies environmental stress to the GIC as in the mouth environment where GIC is used.
(8) Each sample material is immersed in distilled water and is left standing at 37° C. for 23 hours just before the three-point bending test.
Between the immersion and the test, burrs are removed from the sample material with water resistant paper and Evans carver, and the size of the sample material is measured at the central part by using a micrometer (d=0.01 mm).
(9) The three-point bending test is performed by a universal testing machine (Shimadzu AG10TA). The length between two rods that are arranged under the sample material is set 16 mm, and the speed of crosshead is set 0.5 mm/min.
(10) Student's t-test is used for statistically significant difference between the measurement values.
[Results]
The results of the three-point bending test are shown below.
(1) Comparative Example 1 . . . 23.8±2.0 MPa
(2) Comparative Example 2 . . . 24.4±1.0 MPa
(3) Example 1 . . . 37.3±2.7 MPa
(4) Comparative Example 3 . . . 25.6±2.2 MPa
(5) Comparative Example 4 . . . 15.4±1.0 MPa The above results show that GIC according to the example 1 of the present invention has excellent strength as compared with GIC according to the comparative examples 1 to 4.

It can be concluded based on the above results that, in the case where hydroxy apatite is pulverized into ultra-fine particles, and the ultra-fine hydroxy apatite particles is added and mixed into glass powder for GIC, this addition/mixture can improve the flexural strength of chemically-curing type GIC to the same extent as light-curing type GIC.

In addition to this, the three-point bending test is performed on the example 1 and the comparative example 2 under two states, i.e., a dry state and a wet state at 15 minutes after mixture. The conditions and the results of this test are explained below.

Curing and Testing Methods of GIC in Example 1 and Comparative Example 2

(1) IX powder, IX liquid, and HAp are measured by using an electronic balance [manufactured by Satorius Corp. (Germany)].
(2) The measured IX powder and HAp powder are mixed by using an automatic mixer (vortex) for one minute.
(3) A separation material (SURE SEP) is applied on a mold of stainless steel alloy (3.0 mm×3.0 mm×25.0 mm) with a small brush, and is then extended and thinned with air.
(4) The mixed powder and the IX liquid are kneaded by using a plastic spatula on a paper mixing pad for 45 seconds.
(5) Subsequently, this kneaded material is aspirated into a syringe (a kind of injector), and is then injected into the mold. In this process, the mold is pressed by a plugger that brings neither air bubbles nor clearances, then is placed on a glass mixing plate.
(6) The mold is pressed by a weight (500 g) so that a transparent strip is sandwiched between the mold and the weight, and is then left standing for ten minutes at room temperature.
The GIC is cured in this state.
(7) The sample material is picked up from the mold. At 2 minutes and 30 seconds after picked up, in the case of a wet group, the sample material is immersed in distilled water, or in the case of a dry group, the sample material is left standing in a room environment.
This process brings GIC into the wet state or the dry state.
(8) Burrs are removed from the sample material with water resistant paper and Evans carver, and the size of the sample material is measured at the central part by using a micrometer (d=0.01 mm).
(9) The three-point bending test is performed by a universal testing machine (Shimadzu AG10TA). The length between two rods that are arranged under the sample material is set 16 mm, and the speed of Crosshead is set 0.5 mm/min.
[Results]
The results of the three-point bending test are shown below.
(1) Dry State

| | |
|---|---|
| Example 1 | 13.1 ± 7.0 MPa |
| Comparative Example 2 | 8.2 ± 2.2 MPa |

(2) Wet State

| | |
|---|---|
| Example 1 | 16.1 ± 4.5 MPa |
| Comparative Example 2 | 11.1 ± 2.5 MPa |

Based on the above results, GIC according to the example 1 of the present invention that includes HAp100 (fine) as the hydroxy apatite provides excellent strength both in the dry state and in water at 15 minutes after kneaded as compared with GIC according to the comparative example 2 that includes HAp100 as the hydroxy apatite.

In addition to this, chemical analysis is performed on GIC without added HAp, GIC according to the example 1 with added HAp100 (fine), and GIC according to the comparative example 2 with added HAp100 by using a X-ray microanalyzer (EPMA). The results of this analysis are explained below.

[Method]

X-ray microanalyzer (EPMA): Point analysis is performed on a core, HAp and the matrix portion of each sample material that are observed by SEM by using EPMA (Link Pentafet OXFORD). As the sample material to be used for this analysis, the sample material that has been used to be fractured in the aforementioned three-point bending test is used. The fractured part is analyzed.

In analysis, the matrix portion of GIC is extracted as follows.

(1) Kneaded cement is injected with a syringe into a stainless steel alloy mold with diameter of 6 mm and thickness of 2 mm.
(2) A transparent strip (celluloid strip GC) is placed on the mold. The mold is turned upside down and is placed on a glass mixing plate. Then, a 500 g weigh is placed on the mold to hold down the mold from the top side.
(3) The sample material is left standing until cured (30 minutes), and is then picked up from the mold.
(4) A layer of only the matrix is formed in the top layer of the sample material that has been in contact with the transparent strip.

In the matrix portion that has been extracted by the aforementioned method, Al, Si and Ca are detected which are included in this matrix portion. The ratios (%) of the contents of these elements are calculated and compared. The results are as follows.

(1) The matrix portion of GIC into which HAp is not added

| Al | 43.9 ± 1.0% |
|---|---|
| Si | 55.8 ± 0.6% |
| Ca | 0.3 ± 0.3% |
| Total | 100% |

(2) HAp which is added into GIC

| Al | 12.7 ± 1.8% |
|---|---|
| Si | 11.2 ± 1.0% |
| Ca | 76.1 ± 2.6% |
| Total | 100% |

(3) The matrix portion of GIC according to the example 1 into which HAp100 (fine) is added

| Al | 38.2 ± 0.7% |
|---|---|
| Si | 46.1 ± 1.3% |
| Ca | 15.7 ± 1.7% |
| Total | 100% |

(4) The matrix portion of GIC according to the comparative example 2 into which HAp100 is added

| Al | 40.2 ± 1.0% |
|---|---|
| Si | 54.5 ± 1.1% |
| Ca | 5.3 ± 1.8% |
| Total | 100% |

The above results show that, in GIC of the example 1, reaction of porous HAp with GIC occurs even in a deep region of the GIC. In the case of GIC, little Ca is contained. In addition to this, in the case of HAp, a large amount of Ca is contained. For this reason, since, in the case of the matrix portion of GIC according to the example 1, a comparatively large amount, 15.7% of Ca is contained, it is concluded that Ca of HAp reacts with the matrix portion of GIC. On the other hand, in the case of the matrix portion of GIC according to the comparative example 2, the content of Ca is 5.3%. This content is smaller. For this reason, in the case of the matrix portion of GIC according to the comparative example 2, although HAp is added, Ca of HAp does not effectively react in the matrix portion of GIC.

Additionally, in the case of the HAp added into GIC, the contents of Al and Si rise which are not contained in HAp before reaction. For this reason, it is concluded that, in the case of HAp100 (fine) that is porous and has a particular particle diameter, the reaction with glass ionomer cement occurs even in the deep region. In other words, these results clearly show that, in the matrix portion, Al and Si of GIC move to and react with HAp, and Ca of HAp moves to and reacts with GIC so that GIC and HAp effectively react with each other.

In addition to the aforementioned analysis, X-ray spectrometry (XPS) is performed on GIC of each of the example 1 and the comparative examples 2 and 3 for elementary analysis to analyze the content of Ca. The results are as follows. In this X-ray spectrometry, elements of the matrix portion of GIC are analyzed.

[Method]

Quantitative elementary analysis is performed on the matrix of the sample material by using a X-ray spectrometer (ESCA-1000AX, Shimazu) under the conditions of Mg—Kα as X-ray source and output of 10 keV and 30 mA. The surface of the sample material is etched by Ar-sputtering under the conditions of Ar gas pressure of $5 \times 10^{-4}$ Pa, emission voltage and current of 2 keV and 20 mA to perform depth-directional analysis. The etching rate is 20 Å ($Al_2O_3$) per minute. In this analysis, elements to be analyzed are C, O, F, Al, Si, P and Ca.

[Results]

As for the content of Ca in the matrix portion of GIC according to the example 1, the analysis results in Comparative Example 3<Comparative Example 2<Example 1. Ca of the GIC matrix portion according to the example 1 is increased. This analysis shows that, in the case of the GIC according to the example 1, Ca of added HAp effectively reacts with GIC. That is, the reason is that Ca contained in HAp reacts with GIC so that Ca of the matrix portion is increased.

Also, this shows that addition of particular HAp produces a unprecedented, new type matrix that containing P and Ca. Also, it is seen that as Ca is increased which is contained in GIC the flexural strength of the GIC is improved. As compared with GIC according to the comparative example 3 in that crystalline HAp200 group is employed as hydroxy apatite, in the case of the GIC matrix portion according to the example 1 in that porous HAp with the particular particle diameter is employed, reaction with cement liquid occurs better. As a result, the flexural strength of the GIC matrix portion according to the example 1 is improved.

Example 2

Addition/Mixture Amount of Apatite Relative to GIC Glass Powder

[Material and Method]

A method similar to the example 1 described above is conducted by using IX powder, IX liquid, and HAp100 (fine). That is, HAp100 (fine) is mixed at 5% by weight, 8% by weight, 11% by weight, 16% by weight, 19% by weight, 25% by weight, 30% by weight, and 35% by weight relative to IX powder, After thus prepared, the mixed sample powder is kneaded with IX liquid at a P/L rate of 3.6. At 24 hours after the kneading process, the three-point bending test is performed. The results of this three-point bending test are as follows.

[Results]

In the cases of the mixture amounts (% by weight) of HAp100 (fine) relative to IX powder, the results of this three-point bending test (measurement values MPa) are as follows.

| | |
|---|---|
| 5% by weight | 27.5 MPa |
| 8 to 30% by weight | 35 to 40 MPa |
| 35% by weight | 28.1 MPa |

It is concluded based on the above results that addition/mixture of HAp100 (fine) at about 5% by weight to about 30% by weight relative to GIC glass powder can effectively reinforce or improve mechanical strength without loss of clinical-dentistry-available operability.

Glass ionomer cement according to the present invention includes particular HAp that is added into chemically-curing type GIC. On the other hand, when the HAp is added not into chemically-curing type GIC but into photo-polymerized type glass ionomer cement that is cured by light exposure, the improvement effect by HAp addition cannot be obtained. This is explained as below.

As a material of photo-polymerized type glass ionomer cement, GC FUJI IILC EM (manufactured by GC Corp. hereinafter referred to as IILC EM) is employed which is light-curing type, filling resin reinforcement glass ionomer cement. In this test sample group, HAp100 (fine), which is used in the example 1, is mixed into IILC EM powder at ratios of 8% by weight, 12% by weight, and 16% by weight. Thus, sample powder is obtained. In all the cases, the ratio of powder to liquid is 3.0. This kneaded cement is injected into the mold of 25 mm×3 mm×3 mm, and is left standing at room temperature for ten minutes to be cured. After that, the cement is stored at temperature of 37° C. and humidity of 100% for 50 minutes for 23 hours. After that, the cement is stored in water at 37° C. After that, the three-point bending test is performed on the cement by using the universal testing machine under conditions of Crosshead speed 0.5 mm/min, and span length of 16 mm. (N=6).

The results are as follows.
(1) Light-curing type GIC without added HAp 43.4±6.0 MPa
(2) GIC with 8% by weight of added HAp 40.4±9.5 MPa
(3) GIC with 12% by weight of added HAp 43.6±8.1 MPa
(4) GIC with 16% by weight of added HAp 40.5±10.8 MPa The above results show that, in the case of light-curing type glass ionomer cement, the effects of HAp addition according to the present invention cannot not be expected at all.

INDUSTRIAL APPLICABILITY

Materials for therapy and regeneration of teeth, bones and the like in dentistry, medicine and the veterinary medicine fields. For information, GIC is widely used as dental materials such as a filling material, an abutment construction material, an adhesive material for milk tooth caries, immature permanent tooth caries and root caries of elderly people. In addition to this, WHO uses GIC as a material for dental caries without teeth scraping by nurses or the like in Southeast Asia or Africa. Accordingly, it can be conceived that chemically-curing type GIC with high mechanical strength that is provided by this invention will spread more widely in the future than today in dental care over the world, and will be in the mainstream of use. In addition to this, recently, the use of GIC material already has been contemplated as bone cement in the orthopedics and brain surgery fields. It can be expected that the use of GIC will spread in the medicine and the veterinary medicine field markets.

Figure 1:
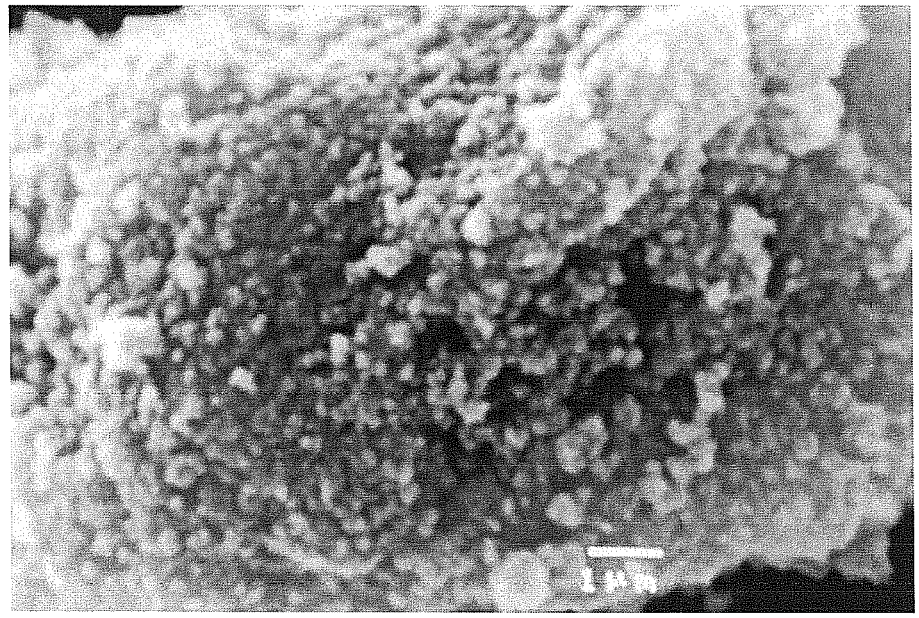
FIG. 1 shows electronic microscopic picture of HAp100 used in a comparative example 2.
Figure 2:
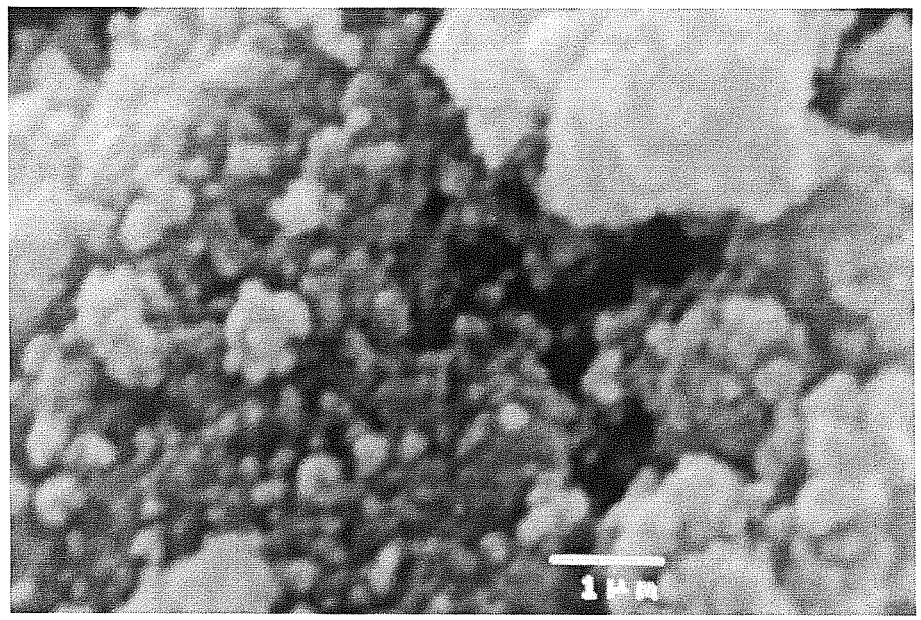
FIG. 2 shows electronic microscopic picture of HAp100 (fine) used in an example 1.
Figure 3:
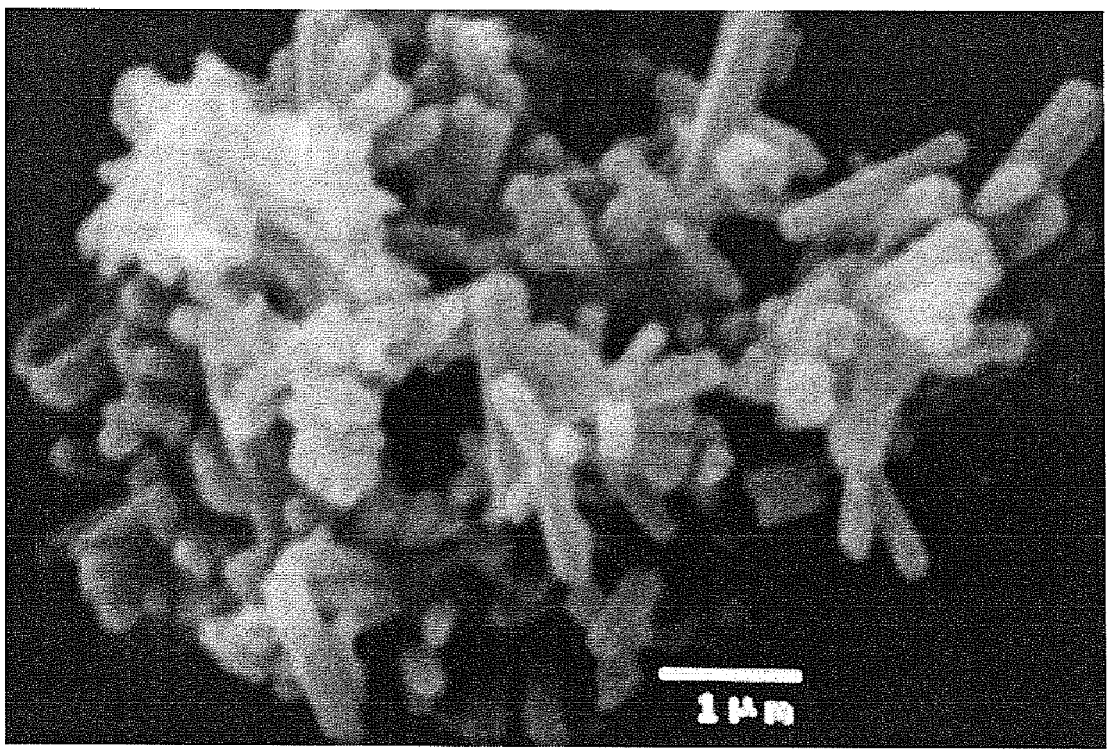
FIG. 3 shows electronic microscopic picture of HAp200 used in a comparative example 3.

The invention claimed is:

1. Chemically-curing type glass ionomer cement comprising porous and particulate hydroxy apatite that has a mean diameter of not less than 0.6 μm and less than 100 μm, and is added and mixed thereinto.

2. Chemically-curing type glass ionomer cement comprising porous and particulate hydroxy apatite that has a mean diameter of not less than 0.6 μm and less than 100 μm, and is added and mixed thereinto, wherein ultra-fine hydroxy apatite particles are adhered on the surface of said hydroxy apatite.

3. The chemically-curing type glass ionomer cement according to claim 1, wherein the glass ionomer cement includes glass powder for glass ionomer cement, and the amount of the added and mixed hydroxy apatite is 5.0 to 35% by weight relative to this glass powder.

4. The chemically-curing type glass ionomer cement according to claim 1, wherein the glass ionomer cement is adapted for dentistry.

5. The chemically-curing type glass ionomer cement according to claim 1, wherein the glass ionomer cement is adapted for bone therapy in medicine and veterinary medicine fields.

6. The chemically-curing type glass ionomer cement according to claim 1, wherein the glass ionomer cement is adapted for bone tissue restoration or regeneration.

7. A method comprising:
performing dentistry using the chemically-curing type glass ionomer cement according to claim 1.

8. A method comprising:
performing bone therapy in medicine or veterinary medicine fields using the chemically-curing type glass ionomer cement according to claim 1.

9. A method comprising:
performing bone tissue restoration or regeneration using the chemically-curing type glass ionomer cement according to claim 1.

* * * * *

UNITED STATES PATENT AND TRADEMARK OFFICE
CERTIFICATE OF CORRECTION

PATENT NO. : 8,083,844 B2  
APPLICATION NO. : 12/298154  
DATED : December 27, 2011  
INVENTOR(S) : Arita Page 1 of 1

It is certified that error appears in the above-identified patent and that said Letters Patent is hereby corrected as shown below:

Title page, the INID (22) should read as follows:
(22) PCT Filed:  Apr. 24, 2007

Signed and Sealed this
Fifteenth Day of May, 2012

David J. Kappos
*Director of the United States Patent and Trademark Office*